United States Patent
Timothy et al.

(10) Patent No.: US 12,369,959 B2
(45) Date of Patent: Jul. 29, 2025

(54) SCREW WITH AN IMPROVED SCREW HEAD

(71) Applicant: PrimeSource Building Products, Inc., Irving, TX (US)

(72) Inventors: E Erik Timothy, Apollo Beach, FL (US); Chih-Hsien Shen, Kaohsiung (TW); Tse-Kuang Jou, Kaohsiung (TW)

(73) Assignee: PRIMESOURCE BUILDING PRODUCTS, INC., Irving, TX (US)

( * ) Notice: Subject to any disclaimer, the term of this patent is extended or adjusted under 35 U.S.C. 154(b) by 347 days.

(21) Appl. No.: 18/082,905

(22) Filed: Dec. 16, 2022

(65) Prior Publication Data

US 2024/0197376 A1    Jun. 20, 2024

(51) Int. Cl.
*A61B 17/86* (2006.01)

(52) U.S. Cl.
CPC ........ *A61B 17/8605* (2013.01); *A61B 17/863* (2013.01); *A61B 17/8635* (2013.01)

(58) Field of Classification Search
CPC ........................... A61B 17/862; A61B 17/8605
See application file for complete search history.

(56) References Cited

U.S. PATENT DOCUMENTS

| | | |
|---|---|---|
| 3,903,784 A | 9/1975 | Dekker |
| 4,842,467 A | 6/1989 | Armstrong |
| 5,516,248 A | 5/1996 | Dehaitre |
| 6,109,850 A | 8/2000 | Commins |
| 6,558,097 B2 | 5/2003 | Mallet et al. |
| 7,160,073 B2 | 1/2007 | Mizuno et al. |
| 7,293,947 B2 | 11/2007 | Craven |
| D557,130 S | 12/2007 | Kashikura et al. |
| D557,131 S | 12/2007 | Liu |
| 7,334,976 B2 | 2/2008 | Dicke |
| D567,644 S | 4/2008 | Liu |
| 7,988,396 B2 | 8/2011 | Weiss et al. |
| 8,231,320 B2 | 7/2012 | Hettich |
| 8,337,131 B2 | 12/2012 | Hettich |
| 8,430,618 B2 | 4/2013 | Baer et al. |
| 8,616,816 B2 | 12/2013 | Pieciak, Jr. et al. |
| 8,647,038 B2 | 2/2014 | Gong et al. |
| 8,858,145 B2 | 10/2014 | Su et al. |
| 9,234,539 B2 | 1/2016 | Gonciarz et al. |

(Continued)

FOREIGN PATENT DOCUMENTS

| | | |
|---|---|---|
| AU | 2018101598 A4 | 11/2018 |
| CN | 101498334 A | 8/2009 |

(Continued)

OTHER PUBLICATIONS

Jones, H.K., U.S. Pat. No. 471,179A, Issued Mar. 22, 1892.

*Primary Examiner* — Olivia C Chang
(74) *Attorney, Agent, or Firm* — Husch Blackwell LLP (57) ABSTRACT

A screw with an improved screw head is provided. The screw may include a shank in between a head and a tip. The head may include a plurality of protrusions provided radially along the head. Each of the plurality of protrusions may include a protrusion wall, a leading wall, a trailing wall, and a bottom wall; the trailing wall may include one single trailing surface, the leading wall may include a plurality of leading surfaces, and the bottom wall may include at least one bottom surface.

14 Claims, 10 Drawing Sheets

(56) References Cited

U.S. PATENT DOCUMENTS

| | | |
|---|---|---|
| 9,377,045 B2 | 6/2016 | Su et al. |
| 9,506,490 B2 | 11/2016 | Scheerer |
| 9,581,183 B2 | 2/2017 | Lajewardi et al. |
| 9,581,184 B2 | 2/2017 | Ban |
| 9,624,961 B2 | 4/2017 | Lin |
| 9,719,545 B2 | 8/2017 | Hsu |
| 9,970,470 B2 | 5/2018 | Shih |
| 10,054,148 B2 | 8/2018 | Lin |
| D840,796 S | 2/2019 | Hsiao |
| 10,247,219 B2 | 4/2019 | Lajewardi et al. |
| 10,309,437 B2 | 6/2019 | Lin |
| D853,830 S | 7/2019 | Wang |
| D854,404 S | 7/2019 | Wang |
| D863,050 S | 10/2019 | Chao |
| 10,436,238 B2 | 10/2019 | Falkenstein et al. |
| 10,480,559 B2 | 11/2019 | Park |
| 10,480,562 B2 | 11/2019 | Shih |
| 10,626,909 B2 | 4/2020 | Huang |
| 10,662,994 B2 | 5/2020 | Scheerer et al. |
| D885,874 S | 6/2020 | Hsiao |
| D888,545 S | 6/2020 | Dissing |
| 10,801,539 B2 | 10/2020 | Su et al. |
| 10,954,986 B2 | 3/2021 | Ruhmann et al. |
| 10,954,989 B2 | 3/2021 | Lucas |
| 11,105,361 B2 | 8/2021 | Lajewardi et al. |
| 11,149,776 B2 | 10/2021 | Hu |
| 11,181,138 B2 | 11/2021 | Park |
| 11,293,475 B2 | 4/2022 | Hsu et al. |
| 11,346,388 B2 | 5/2022 | Dissing |
| 11,359,661 B2 | 6/2022 | Dissing |
| 2013/0011214 A1 | 1/2013 | Lin |
| 2017/0284447 A1* | 10/2017 | Falkenstein ........... F16B 23/003 |
| 2019/0136897 A1* | 5/2019 | Lajewardi ........... F16B 25/0052 |
| 2020/0056647 A1 | 2/2020 | Su |
| 2021/0204991 A1* | 7/2021 | Epstein .............. A61B 17/8605 |
| 2021/0222723 A1* | 7/2021 | Hsu .................... F16B 25/0047 |
| 2022/0056942 A1 | 2/2022 | Dissing |
| 2022/0090621 A1 | 3/2022 | Shih |

FOREIGN PATENT DOCUMENTS

| | | |
|---|---|---|
| CN | 102235410 A | 11/2011 |
| CN | 202182094 U | 4/2012 |
| CN | 203362767 U | 12/2013 |
| CN | 203979057 U | 12/2014 |
| CN | 102996595 B | 8/2015 |
| CN | 204851918 U | 12/2015 |
| CN | 104948555 B | 4/2018 |
| CN | 107906104 A | 4/2018 |
| CN | 209083764 U | 7/2019 |
| CN | 209228826 U | 8/2019 |
| CN | 110319100 A | 10/2019 |
| CN | 211039335 U | 7/2020 |
| CN | 211059174 U | 7/2020 |
| CN | 213331938 U | 6/2021 |
| CN | 113251051 A | 8/2021 |
| CN | 215805646 U | 2/2022 |
| CN | 215861221 U | 2/2022 |
| CN | 216922780 U | 7/2022 |
| CN | 217029566 U | 7/2022 |
| DE | 9106746 U1 | 7/1991 |
| DE | 102011008167 A1 | 7/2012 |
| EP | 0705987 B1 | 8/2002 |
| EP | 1806508 B1 | 12/2009 |
| EP | 1820978 B1 | 4/2010 |
| EP | 1903224 B1 | 2/2012 |
| EP | 2522865 B1 | 8/2014 |
| EP | 2811181 B1 | 7/2017 |
| EP | 3006748 B1 | 11/2018 |
| EP | 3121462 B1 | 9/2019 |
| EP | 3569878 B1 | 12/2020 |
| EP | 3550160 B1 | 3/2021 |
| EP | 3855026 A1 | 7/2021 |
| EP | 3625465 B1 | 9/2021 |
| FR | 2827349 B3 | 6/2003 |
| FR | 2950664 B1 | 10/2012 |
| GB | 2304849 B | 7/1999 |
| JP | 3298859 B2 | 7/2002 |
| JP | 2003130023 A | 5/2003 |
| TW | M375788 U | 3/2010 |
| TW | M429779 U | 5/2012 |
| TW | M443787 U | 12/2012 |
| TW | I496997 B | 8/2015 |
| TW | I507614 B | 11/2015 |
| TW | I701391 B | 8/2020 |
| WO | 2021/009608 A1 | 1/2021 |

* cited by examiner

FIG. 11

SCREW WITH AN IMPROVED SCREW HEAD

FIELD OF THE INVENTION

This disclosure generally relates to a fastener. More particularly, this disclosure relates to a screw with an improved screw head design.

BACKGROUND OF THE INVENTION

As a screw is fastened into a board, in may be desirable to have the screw countersink into the board. Generally, a countersunk screw may include a flat head, such that the head may sit flush on a top surface of the board after the screw is fastened into the board.

However, as the screw is fastened into the board, debris may be generated. A flat head screw may not specifically be designed to accommodate such debris. Thus, there is a need for a screw head design that may better accommodate debris.

Moreover, it may be desirable to have a screw head design that improves a performance of the screw, such as to increase grip after the screw has been fastened into the board. Thus, there are further needs for a better screw head design.

BRIEF SUMMARY OF THE INVENTION

A first aspect of this disclosure pertains to a screw comprising a shank in between a head and a tip, wherein the head includes a plurality of protrusions provided radially along the head, wherein each of the plurality of protrusions includes a protrusion wall, a leading wall, a trailing wall, and a bottom wall.

A second aspect of this disclosure pertains to the screw of the first aspect, wherein the trailing wall comprises one single trailing surface.

A third aspect of this disclosure pertains to the screw of the first aspect, wherein the leading wall comprises a plurality of leading surfaces.

A fourth aspect of this disclosure pertains to the screw of the first aspect, wherein the bottom wall comprises a plurality of bottom surfaces.

A fifth aspect of this disclosure pertains to the screw of the fourth aspect, wherein at least one of the plurality of bottom surfaces is parallel to a top surface of the head.

A sixth aspect of this disclosure pertains to the screw of the first aspect, wherein the tip includes a flute.

A seventh aspect of this disclosure pertains to the screw of the first aspect, wherein the shank includes a first portion having a first thread, a second portion having a smooth exterior surface, a third portion have a knurled surface, and a fourth portion having a smooth exterior surface.

An eighth aspect of this disclosure pertains to the screw of the seventh aspect, wherein the first portion is provided between the second portion and the tip; wherein the second portion is provided between the first portion and the third portion; wherein the third portion is provided between the second portion and the fourth portion; and wherein the fourth portion is provided between the head and the third portion.

A ninth aspect of this disclosure pertains to the screw of the eighth aspect, wherein the tip includes a second thread.

A tenth aspect of this disclosure pertains to the screw of the ninth aspect, wherein the first thread and the second thread together form one continuous thread.

An eleventh aspect of this disclosure pertains to the screw of the seventh aspect, wherein the first thread includes a plurality of notches.

A twelfth aspect of this disclosure pertains to the screw of the eleventh aspect, wherein the plurality of notches are provided on the first thread in a helical pattern.

A thirteenth aspect of this disclosure pertains to the screw of the first aspect, wherein the head includes a plurality of frustoconical portions such that each successive frustoconical portion has a diameter smaller than a previous frustoconical portion.

A fourteenth aspect of this disclosure pertains to the screw of the thirteenth aspect, wherein the plurality of protrusions each extends downwardly from a top surface of the head and extends outwardly from at least one of the plurality of frustoconical portions.

A fifteenth aspect of this disclosure pertains to the screw of the fourteenth aspect, wherein a radius portion is provided in between two of the plurality of frustoconical portions.

A sixteenth aspect of this disclosure pertains to the screw of the first aspect, wherein the protrusion wall is frustoconical in shape with an axis that extends through a center of the screw.

A seventeenth aspect of this disclosure pertains to a screw comprising a tip having a first thread and a flute; a shank having a first portion including a second thread; a second portion having a smooth exterior, a third portion having a knurled surface, and a fourth portion having a smooth exterior; and a head having a plurality of protrusions provided radially along the head, each of the plurality of protrusions comprising: a protrusion wall extending downwardly and inwardly from a sidewall of the head; a leading wall extending from a first side of the protrusion wall, the leading wall having a plurality of leading surfaces; a trailing wall extending from a second side of the protrusion wall opposite from the first side, the trailing wall having one single trailing surface; and a bottom wall extending from a third side of the protrusion wall, the bottom wall includes at least one bottom surface that is parallel with a top surface of the head.

An eighteenth aspect of this disclosure pertains to the screw of the seventeenth aspect, wherein the first thread includes a plurality of notches.

A nineteenth aspect of this disclosure pertains to the screw of the eighteenth aspect, wherein the plurality of notches are provided on the first thread in a helical pattern.

A twentieth aspect of this disclosure pertains to the screw of the seventeenth aspect, wherein the protrusion wall is frustoconical in shape with an axis that extends through a center of the screw.

Before explaining the disclosed embodiment of the present invention in detail, it is to be understood that the invention is not limited in its application to the details of the particular arrangement shown, since the invention is capable of other embodiments. Exemplary embodiments are illustrated in referenced figures of the drawings. It is intended that the embodiments and figures disclosed herein are to be considered illustrative rather than limiting. Also, the terminology used herein is for the purpose of description and not of limitation.

DETAILED DESCRIPTION

While this invention is susceptible of embodiments in many different forms, there are shown in the drawings and will be described in detail herein specific embodiments with the understanding that the present disclosure is an exemplification of the principles of the invention. It is not intended to limit the invention to the specific illustrated embodiments. The features of the invention disclosed herein in the description, drawings, and claims can be significant, both individually and in any desired combinations, for the operation of the invention in its various embodiments. Features from one embodiment can be used in other embodiments of the invention.

As shown in FIGS. 1-11, the embodiments of this disclosure include a screw 100 with an improved screw head. Referring to FIGS. 1-6, the screw 100 may include a head 200, a tip 300, and a shank 400 in between the head 200 and the tip 300.

The tip 300 may be conical or substantially conical in shape such that the tip 300 gradually decreases in diameter the further away it is from the shaft 400 until the tip 300 converges into a single point, defining a first end 102 of the screw 100. A first thread 310 may be provided on the tip 300.

The shank 400 may be cylindrical or substantially cylindrical in shape. The shank 400 may include a diameter that may be uniformed throughout the shank 400. The shank 400 may include a first shank portion 402, a second shank portion 404, a third shank portion 406, and a fourth shank portion 408. The first shank portion 402 of the shank 400 may be provided proximal to the tip 300 and may separate the tip 300 from the second shank portion 404.

A flute 320 may be provided on the tip 300. For example, the flute 320 may be in the form of a "type 17" cut, resulting in a "type 17" point. In other embodiments, the flute 320 may be in the form of a "type 1" cut, a "type 13" cut, a "type 25" cut, a "type F" cut, or other variations thereof. In further embodiments, the flute 320 may be omitted, forming other types of points such as "type A", "type AB", or the likes.

Figure 1:
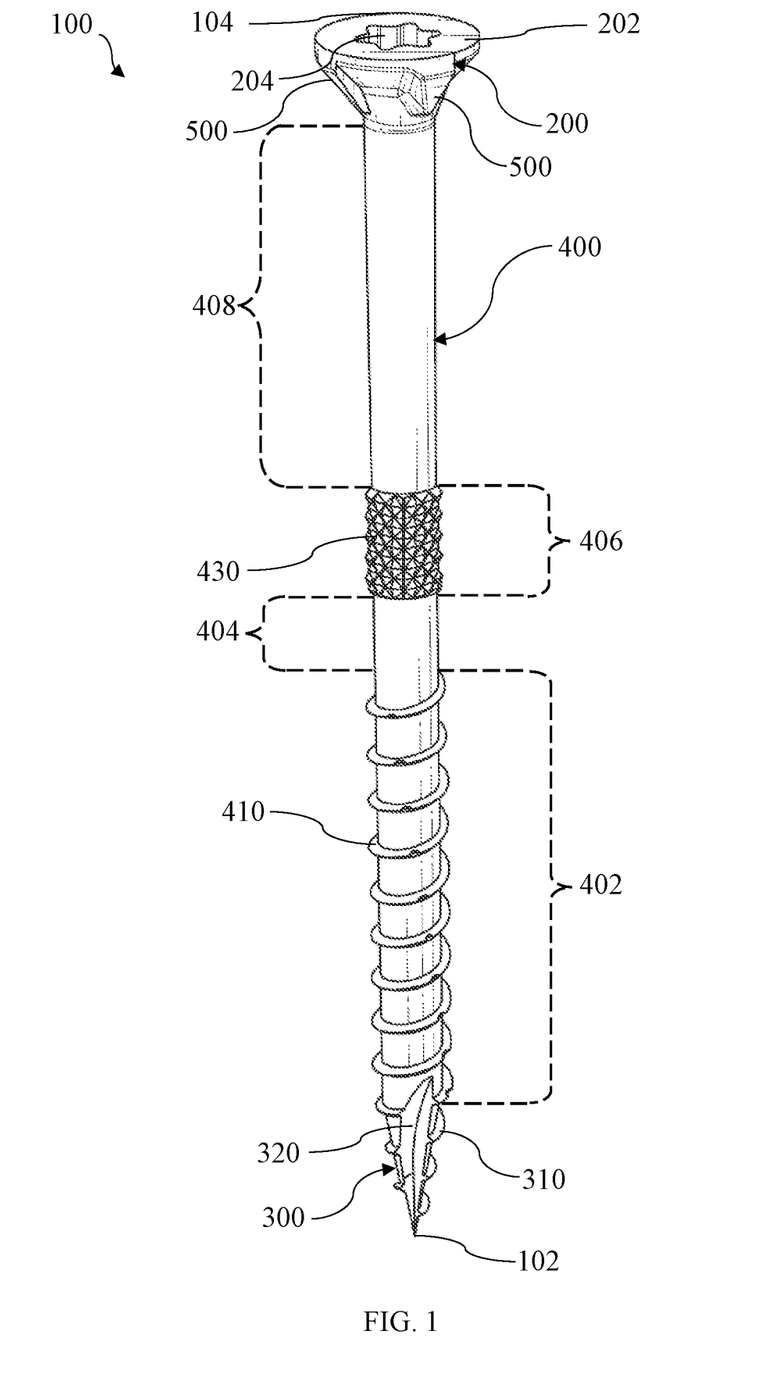
FIG. 1 illustrates an isometric view of a screw according to an embodiment.
Figure 2:
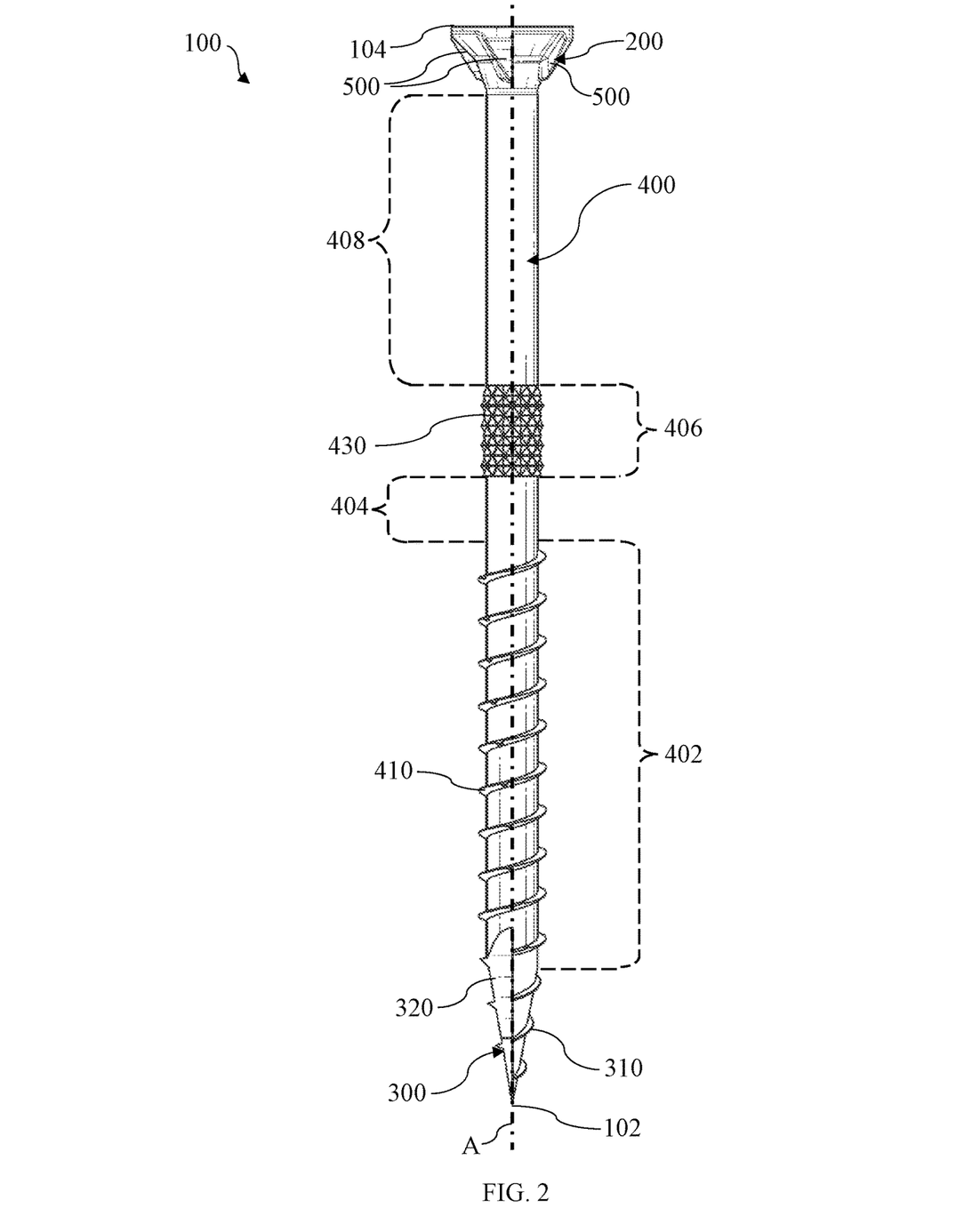
FIG. 2 illustrates another isometric view of the screw of FIG. 1.
Figure 3:
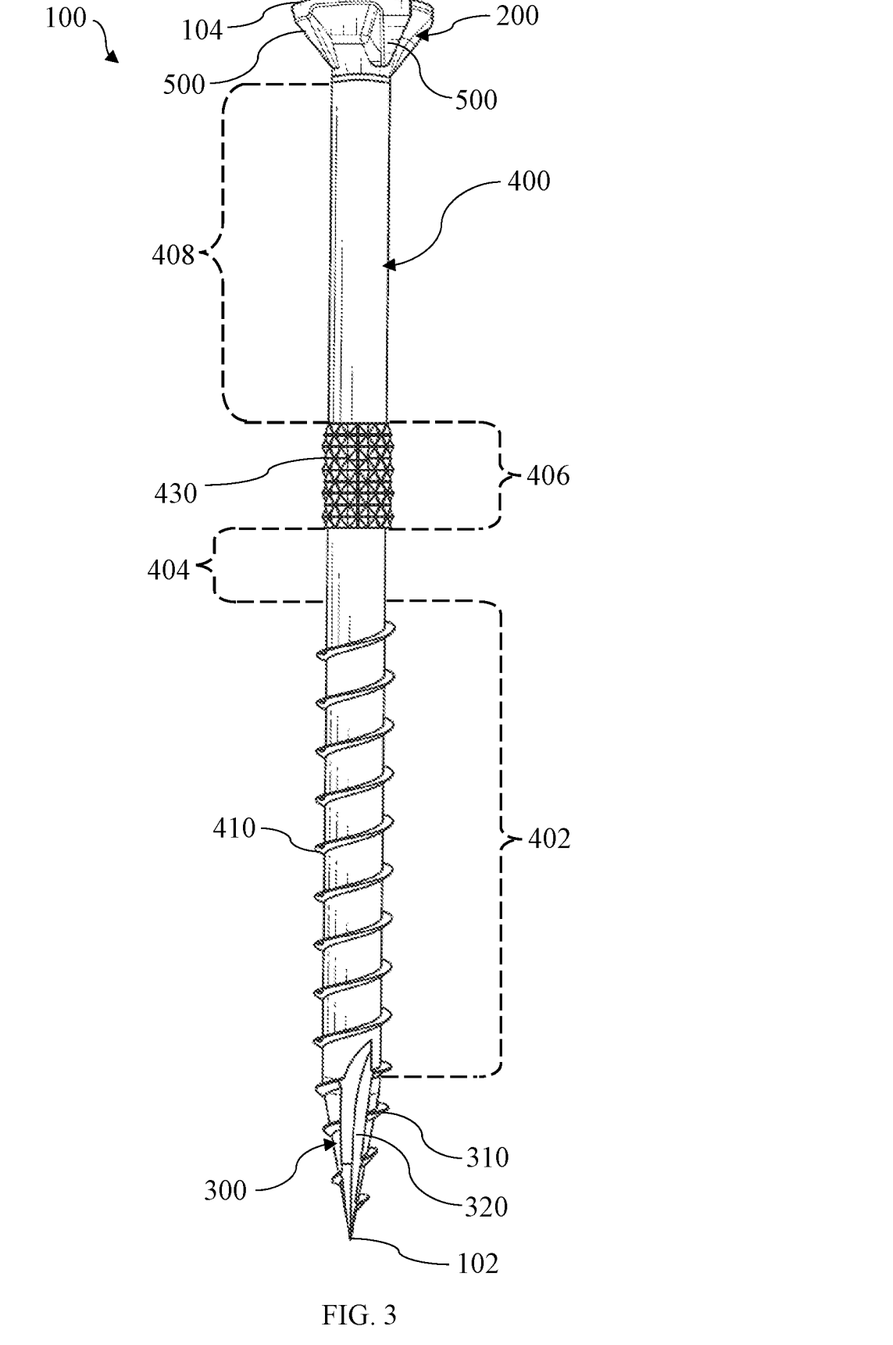
FIG. 3 illustrates another isometric view of the screw of FIG. 1.
Figure 4:
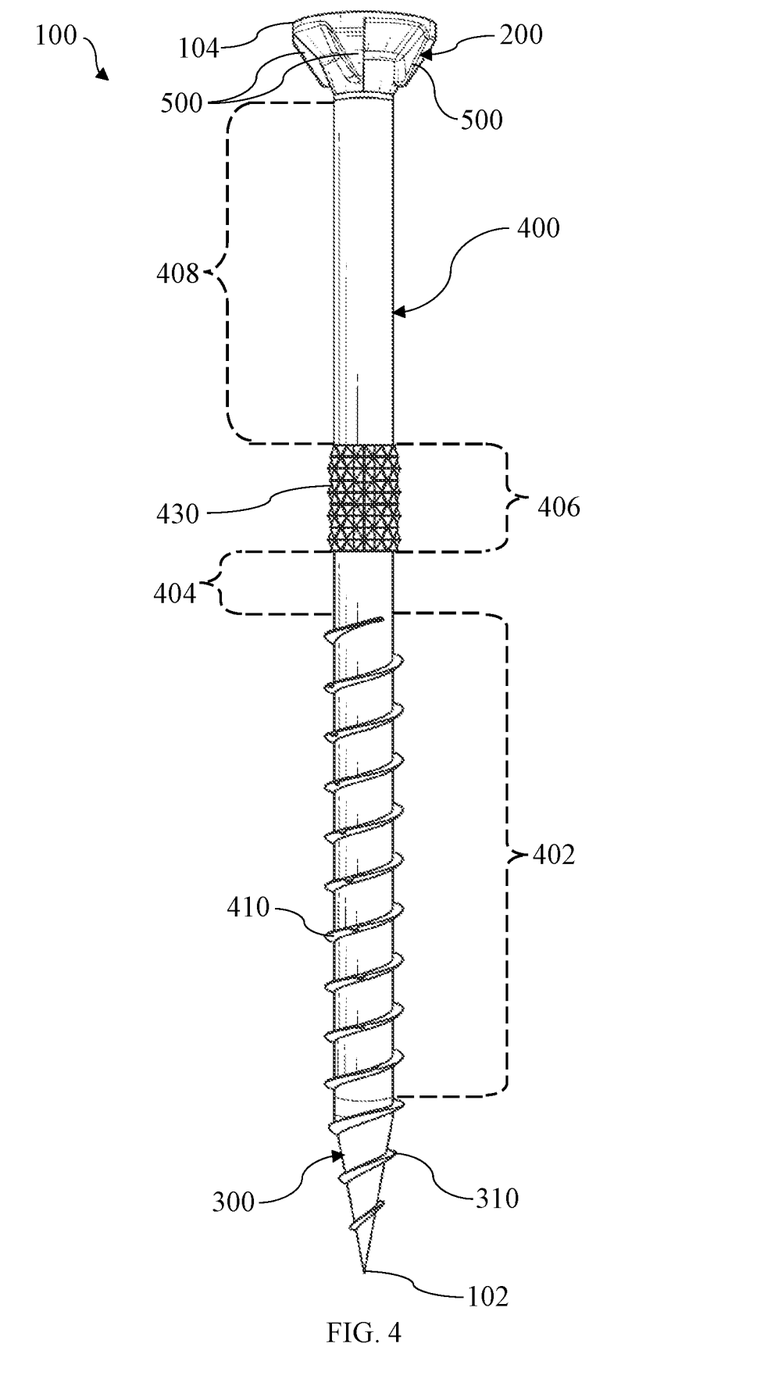
FIG. 4 illustrates another isometric view of the screw of FIG. 1.

As best shown in FIGS. 1-3, the flute 320 may extend from the first end 102 through the tip 300 and partially into the first shank portion 402 of the shank 400. In other embodiments, the flute 320 may be provided solely within the tip 300. In yet further embodiments, the flute 320 may extend through the first shank portion 402 in its entirety. Such and other variations are within the scope of this disclosure.

Figure 8:
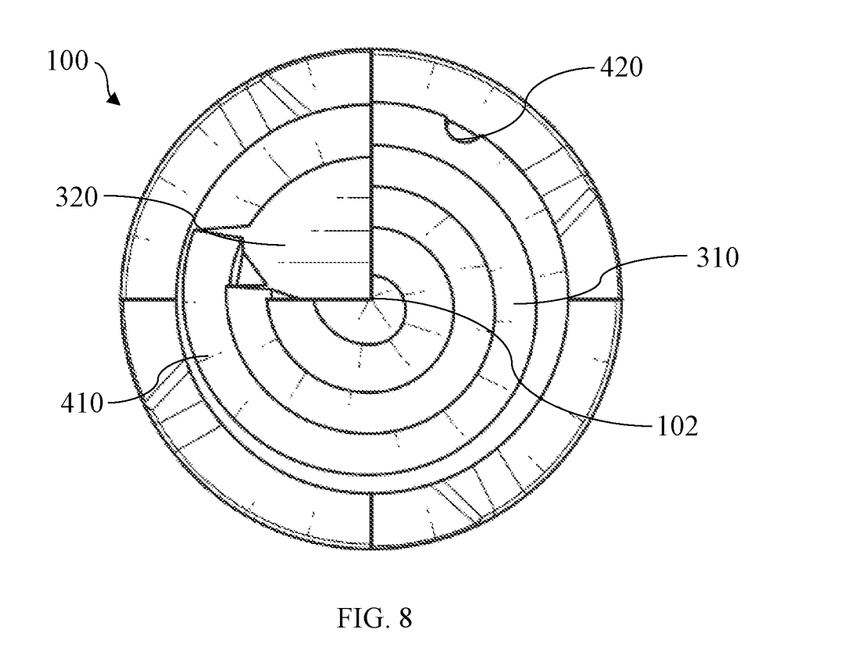
FIG. 8 illustrates a bottom view of the screw of FIG. 1.

In some embodiments, as best shown in FIG. 8, a size of the flute 320 may be approximately a quarter of an overall size of the tip 300. In other embodiment, the flute 320 may be a larger or a smaller proportion of the oversize of the tip 300.

A second thread 410 may be provided on the first shank portion 402. The second thread 410 may extend from the tip 300 to the second shank portion 404. The second thread 410 may be a continuation of the first thread 310, forming a continuous thread from the tip 300 through the first shank portion 402. The second thread 410 and the first thread 310 may share a same or substantially the same pitch and a same or substantially the same thread angle. In other embodiments, the first thread 310 and the second thread 410 may be different and/or may not be not continuous.

Figure 5:
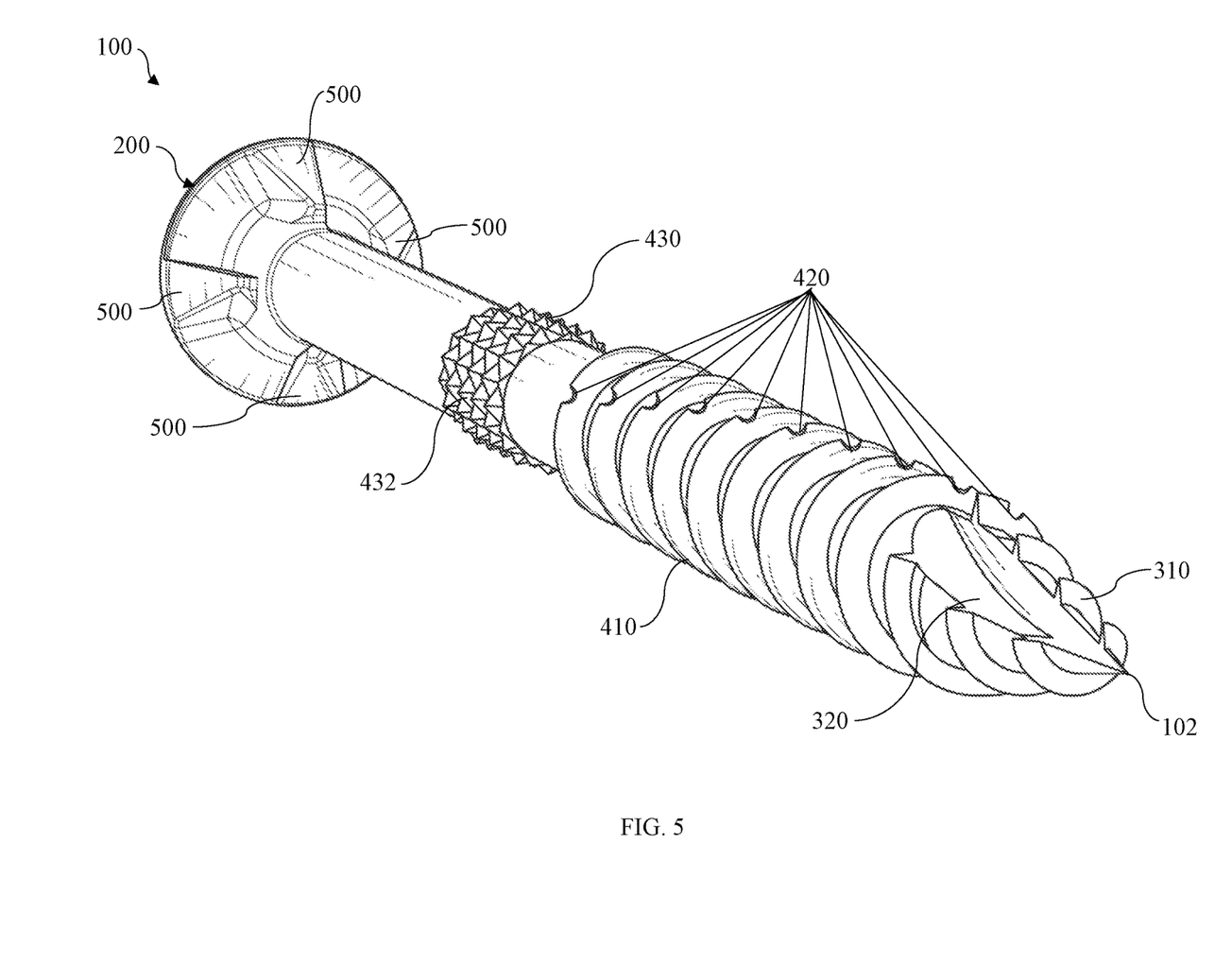
FIG. 5 illustrates another isometric view of the screw of FIG. 1.
Figure 6:
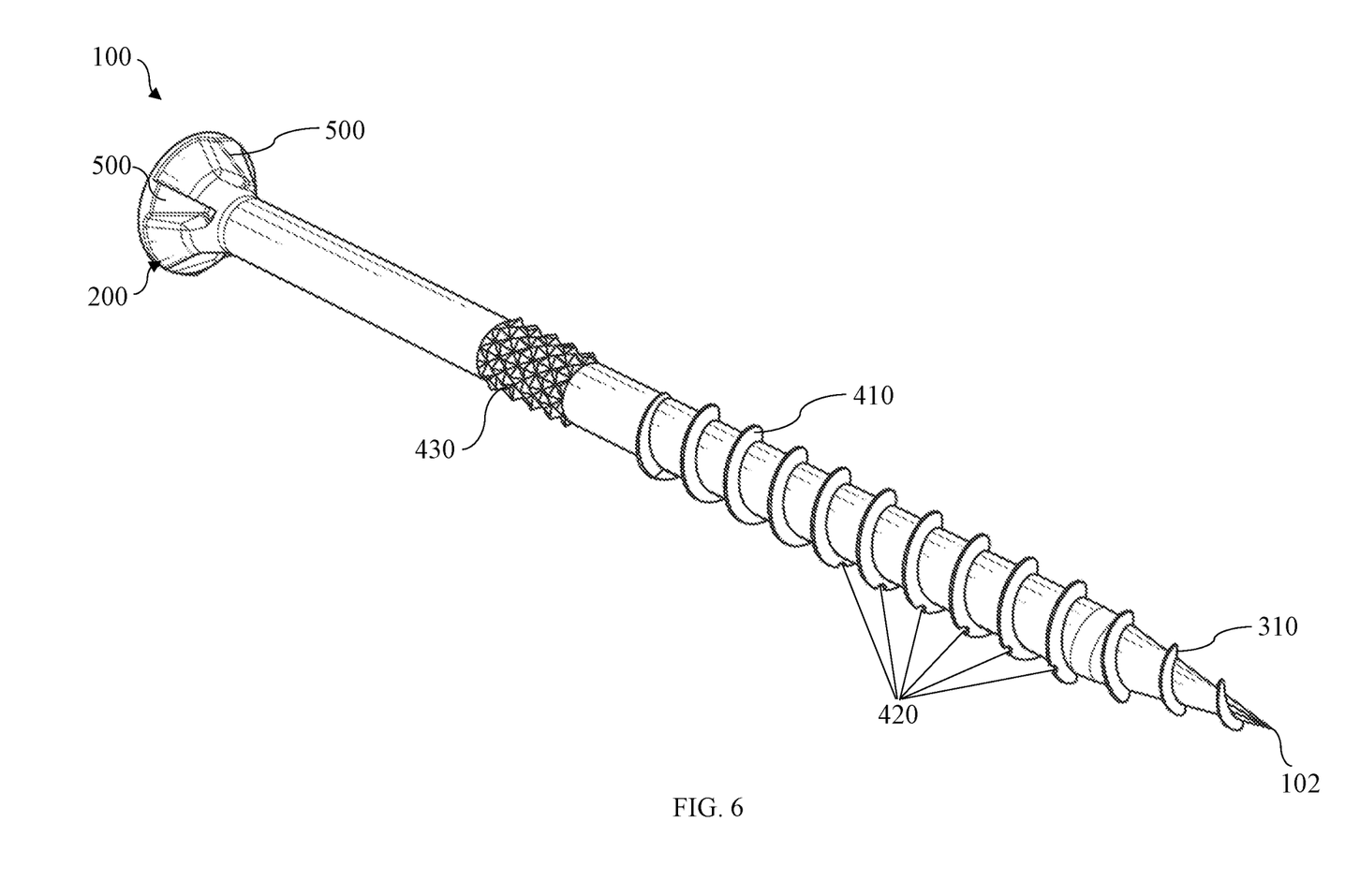
FIG. 6 illustrates another isometric view of the screw of FIG. 1.

As best shown in FIGS. 5 and 6, one or more notches 420 may be provided on the thread 410. The notches 420 may be in the form of indentations in the thread 410. The notches 420 may be provided in a helical pattern such that a location of the notch 420 on the second thread 410 is lightly offset after each pitch. For example, referring to FIG. 5, the notches 420 may be provided on the second thread 410 in a counterclockwise helical pattern. In other embodiments, the notches 420 may be provided in a clockwise helical pattern. In further embodiments, the notches 420 may be provided in a straight-line pattern. Of course, other patterns are also possible and are contemplated herewith.

In some embodiments, the notches 420 may be provided on both the first thread 310 and the second thread 410, only on the second thread 410, only on the first thread 310, or other variations thereof.

The second shank portion 404 of the shank 400 may separate the first shank portion 402 from the third shank portion 406. The second shank portion 404 may be unthreaded and may be provided with a smooth or substantially smooth external surface. In other embodiments, the second thread 410 may extend into the second shank portion 404 either partially or therethrough.

The third shank portion 406 of the shank 400 may separate the second shank portion 404 from the fourth shank portion 408. The third shank portion 406 may include a knurled surface 430 having a plurality of knurls 432 or knots. In some embodiments, the plurality of knurls 432 may be in the form of small polygon protrusions that cover the knurled surface 430.

The fourth shank portion 408 of the shank 400 may be provided proximal to head 200 and may separate the head 200 from the third shank portion 406. The fourth shank portion 408 may be unthreaded and may be provided with a smooth or substantially smooth external surface.

Figure 7:
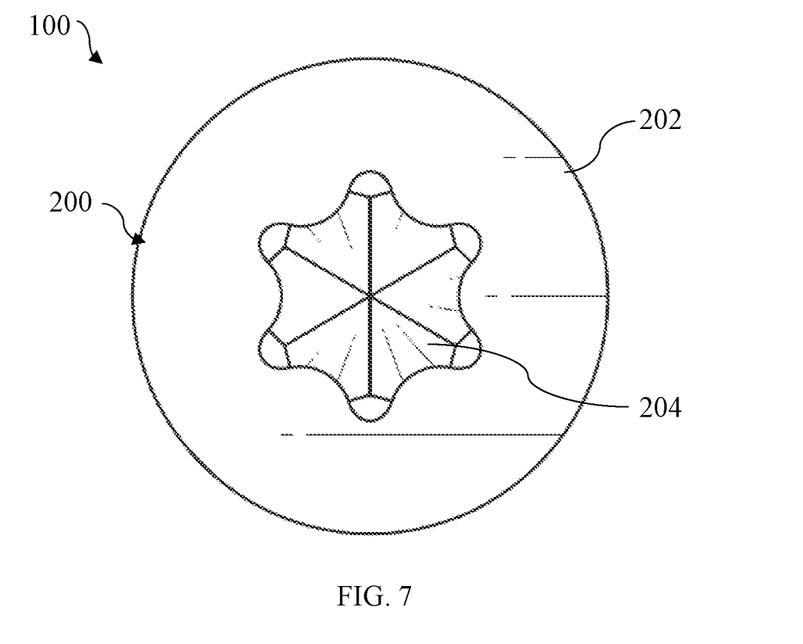
FIG. 7 illustrates a top view of the screw of FIG. 1.

The head 200 may include a top surface 202, defining a second end 104 of the screw 100. The top surface 202 may be circular or substantially circular in shape and may be flat or substantially flat. A drive 204 may be provided on the top surface 202 and may be provided in the form of a cavity that extends inwardly into the head 200 from the top surface 202. In an illustrated embodiment as shown in FIG. 7, the drive 204 may be in the shape of a hexagram. However, other shapes of the drive 204 are also possible and are contemplated herein.

Figure 9:
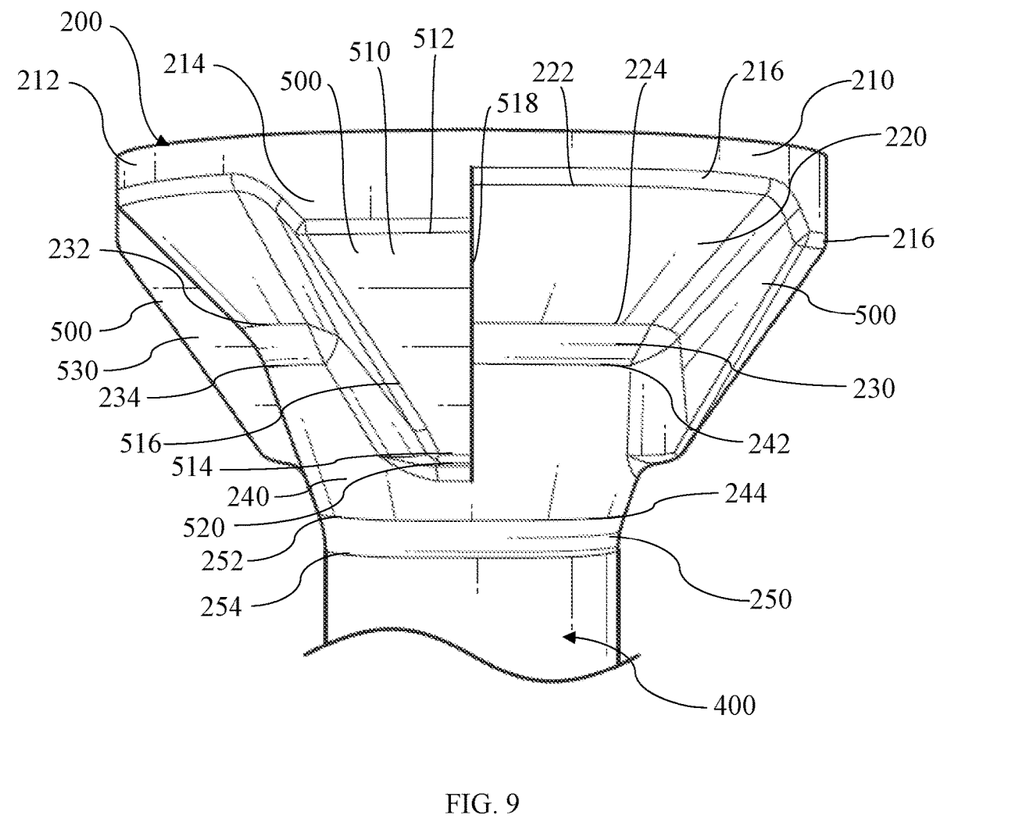
FIG. 9 illustrates an enlarged isometric view of a screw head of the screw of FIG. 1.
Figure 10:
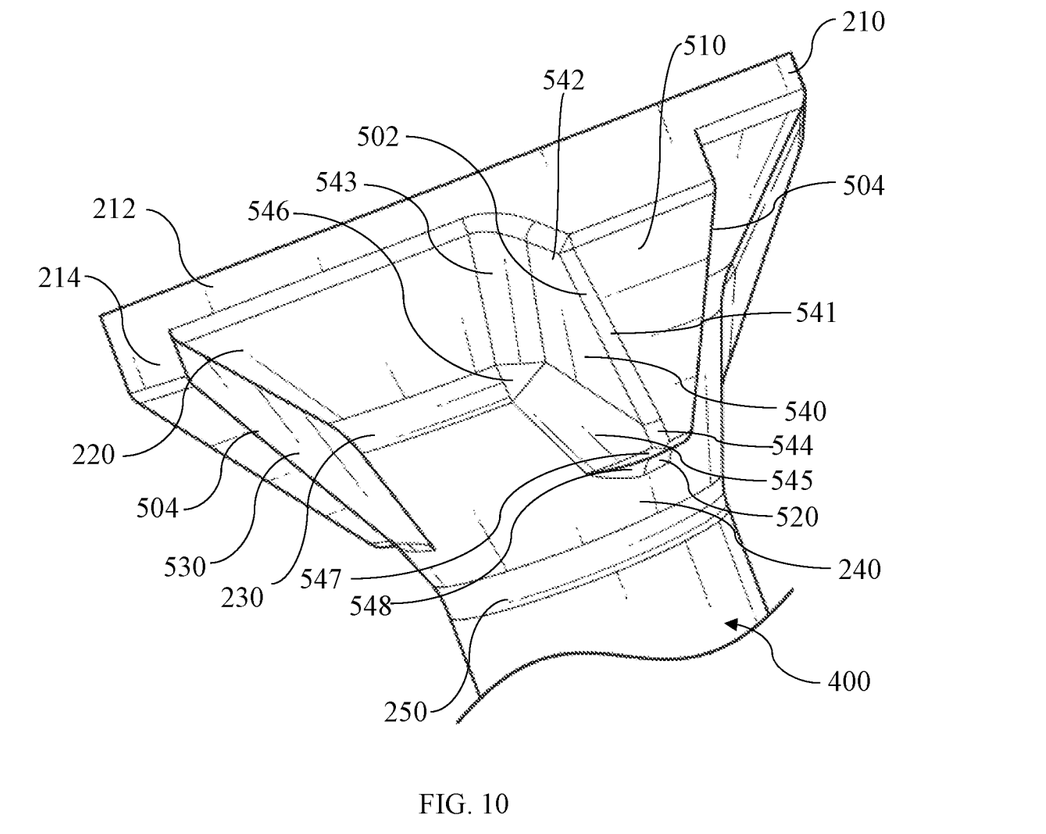
FIG. 10 illustrates another enlarged isometric view of the screw head of FIG. 9.
Figure 11:
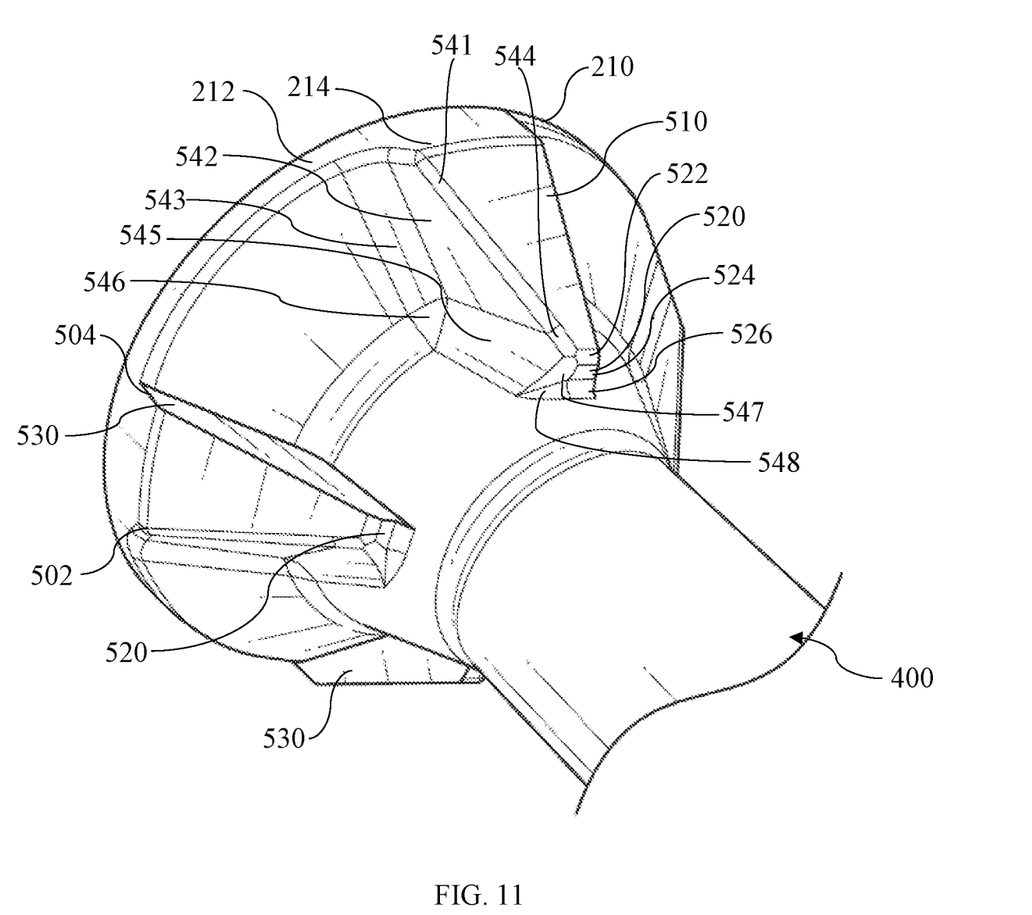
FIG. 11 illustrates another enlarged isometric view of the screw head of FIG. 9.

Referring to FIGS. 9-11, the head 200 may include a sidewall 210 that extends downwardly from the top surface 202 toward the shank 400. The sidewall 210 may be perpendicular or substantially perpendicular to the top surface 202. The sidewall 210 may include a first portion 212 and a second portion 214. The sidewall 210 may extend a first distance downwardly from the top surface 202, forming the first portion 212. Therefrom, portions of the sidewall 210 may continue to extend downwardly until a second distance from the top surface 202, forming the second portion 214. Thus, in some embodiments, the first portion 212 of the sidewall 210 may be provided along the entire circumference of the head 200, while some portions then taper into the second portion 214 of the sidewall 210.

The head 200 may include one or more frustoconical portions such that the head 200 transitions from a first diameter at the top surface 202 to a second diameter that coincide with the diameter of the shank 400.

Referring to FIGS. 9-11, in an illustrated embodiment, the head 200 may include a first radius portion 216, a first frustoconical portion 220, a second radius portion 230, a second frustoconical portion 240, and a third radius portion 250. Each successive frustoconical portion may have a diameter smaller than a previous frustoconical portion and may each include a frustoconical surface.

A radius portion may be provided in between two frustoconical portions, between a frustoconical portion and the shank 400, and/or between a frustoconical portion and the sidewall 210. In some embodiments, the first radius portion 216, the radius portion 230, and/or the third radius portion 250 may each have a radiused surface that be frustoconical in shape. In other embodiment, a shape of the first radius portion 216, the radius portion 230, and/or the third radius portion 250 may vary; other shapes such as cylindrical and other variations thereof are also contemplated herein.

The first frustoconical portion 220 may extend downwardly and inwardly from the first portion 212 of the sidewall 210. A first radius portion 216 may be provided between the first portion 212 and a first end 222 of the first frustoconical portion 220. The first radius portion 216 may extend through an entire edge of the sidewall 210, bordering both the first portion 212 and the second portion 214.

The first end 222 of the first frustoconical portion 220 may be proximal to the top surface 202. The first frustoconical portion 220 may also include a second end 224 distal from the top surface 202. The first end 222 may have a third diameter that is the same as the first diameter (i.e., the diameter of the top surface 202), or a diameter that is smaller than the first diameter. The second end 224 may have a fourth diameter that is smaller than the third diameter. In other embodiments, the fourth diameter may be the same or larger than the third diameter.

The second end 224 of the first frustoconical portion 220 may coincide with a first end 232 of the second radius portion 230, sharing the fourth diameter. The second radius portion 230 may change to a fifth diameter on a second end 234 of the second radius portion 230 distal from the first frustoconical portion 220. The fifth diameter may be smaller than the fourth diameter. In other embodiments, the fifth diameter may be the same or larger than the fourth diameter.

The second end 234 of the second radius portion 230 may coincide with a first end 242 of the second frustoconical portion 240, sharing the fifth diameter. The second frustoconical portion 240 may change to a sixth diameter on a second end 244 of the second frustoconical portion 240 distal from the second radius portion 230. The sixth diameter may be smaller than the fifth diameter. In other embodiments, the sixth diameter may be the same or larger than the fifth diameter.

The second end 244 of the second frustoconical portion 240 may coincide with a first end 252 of the third radius portion 250, sharing the sixth diameter. The third radius portion 250 may change to a seventh diameter on a second end 254 of the third radius portion 250 distal from the second frustoconical portion 240. The seventh diameter may be the same as the second diameter (i.e., the diameter of the shank 400). The seventh diameter may be smaller than the sixth diameter. In other embodiments, the seventh diameter may be the same or larger than the sixth diameter.

A plurality of protrusions 500 may be provided radially along the head 200. The plurality of protrusions 500 may be provided downwardly from the top surface 202, and outwardly from one or more of the frustoconical portions.

The protrusions 500 may each include a leading edge 502, and a trailing edge 504. The leading edge 502 and the trailing edge 504 may be dictated by a rotational direction of the screw 100. For example, if the screw 100 is intended to be screwed in clockwise, the leading edge 502 may be provided on the left side of the protrusions 500 and the trailing edge 504 may be provided on the right side of the protrusions 500. In a further example, if the screw 100 is intended to be screwed in counterclockwise, the leading edge 502 may be provided on the right side of the protrusions 500 and the trailing edge 504 may be provided on the left side of the protrusions 500.

Referring to FIGS. 9-11, the protrusion 500 may include a protrusion wall 510 that may extend downwardly and inwardly from the second portion 214 of the sidewall 210. The first radius portion 216 may be provided in between the protrusion wall 510 and the second portion 214 of the sidewall 210.

The protrusion wall 510 may be trapezoidal in shape and may be flat, substantially flat, or curved (which may resemble a slice of a frustoconical shape). In embodiments where the protrusion wall 510 is frustoconical in shape, the protrusion wall 510 may have an axis A that coincide with a central axis that extends through a center of the screw 100 (see FIG. 2); such a configuration may form a large support surface that mates with a shape of a hole that the head 200 creates in the substrate.

The protrusion wall 510 may include a first side 512, a second side 514, a third side 516, and a fourth side 518. The first side 512 may coincide with a bottom side of the first radius portion 216. The second side 514 may be substantially perpendicular with the first side 512, but may be provided distal from the first radius portion 216. The third side 516 and the fourth side 518 may be provided between the first side 512 and the second side 514, with the third side 516 being opposite from the fourth side 518.

As best shown in FIG. 11, the protrusion 500 may include a bottom wall 520 that extend from the second side 514 of the protrusion wall 510 inwardly toward the second frustoconical portion 240. Referring to FIG. 11, in the illustrated embodiment, the bottom wall 520 may include a first bottom surface 522, a second bottom surface 524, and a third bottom surface 526 are provided. In the illustrated embodiment, the first bottom surface 522 may transition the second side 514 of the protrusion wall 510 toward the second bottom surface 524, such that the second bottom surface 524 may be parallel or substantially parallel to the top surface 202. Therefrom, the third bottom surface 526 may connect the second bottom surface 524 with the second frustoconical portion 240 in a sloped or curved fashion. Thus, in some embodiments, the first bottom surface 522 and the third bottom surface 526 may each faces outwardly away from the screw 100, while the second bottom surface 524 may be parallel to the top surface 202.

Although three bottom surfaces are illustrated in the example embodiment in FIG. 11, it should be appreciated that the bottom wall 520 may include fewer or more bottom surfaces. In some embodiments, only one bottom surface may be provided, which may be parallel or substantially parallel to the top surface 202 or at an angle that connects the second side 514 of the protrusion wall 510 and the second frustoconical portion 240.

The protrusion 500 may include a trailing wall 530 at the trailing edge 504. As best shown in FIG. 11, the trailing wall 530 may be bordered by the second portion 214 of the sidewall 210, the first radius portion 216, the fourth side 518 of the protrusion wall 510, the first bottom surface 522, the second bottom surface 524, the third bottom surface 526, the first frustoconical portion 220, the second radius portion 230, and the second frustoconical portion 240.

The trailing wall 530 may include one singular flat or substantially flat trailing surface. In other embodiments, the trailing wall 530 may include multiple trailing surfaces facing different angles.

As best shown in FIG. 11, a first side 532 of the trailing wall 530 that coincides with the second portion 214 of the sidewall 210 may be biased more toward the trailing edge 504 than a second side 534 of the trailing wall 530 that coincides with the second frustoconical portion 240, thus forming a sharp angle at the trailing edge 504. Put differently, the second side 534 of the trailing wall 530 may be biased more toward the leading edge 502 than the first side 532 of the trailing wall 530. In other embodiments, such bias may be omitted such that the trailing wall 530 may be perpendicular or substantially perpendicular to the second portion 214 of the sidewall 210. In further embodiments, the bias may be reversed, such that the second side 534 is biased away from the leading edge 502, thus forming a blunt angle at the trailing edge 504.

The protrusion 500 may include a leading wall 540 at the leading edge 502. The leading wall 540 may connect the protrusion wall 510 to the first frustoconical portion 220, the second radius portion 230, and the second frustoconical portion 240. The leading wall 540 may include a plurality of leading surfaces. For example, referring to FIG. 10, the leading wall 540 may include a first leading surface 541, a second leading surface 542, and a third leading surface 543 that together transition the protrusion 500 from a top portion of the third side 516 of the protrusion wall 510 to the first frustoconical portion 220.

Likewise, the leading wall 540 may further include a fourth leading surface 544, a fifth leading surface 545, and a sixth leading surface 546 that together transition the protrusion 500 from a bottom portion of the third side 516 of the protrusion wall 510 to the second radius portion 230 and the second frustoconical portion 240.

As best shown in FIG. 11, the leading wall 540 may also include a seventh leading surface 547 and an eighth leading surface 548 that together transition the protrusion 500 from the bottom wall 520 to other leading surfaces of the leading wall 540 (such as the fourth leading surface 544 and the fifth leading surface 545). In some embodiments, the plurality of leading surfaces that form the leading wall 540 may each face a different plane at different angles. In other embodiments, some of the plurality of leading surfaces that form the leading wall 540 may face a same plane.

As explained above, in some embodiments, the trailing wall 530 may include one singular trailing surface, resulting in the trailing edge 504 being relatively sharp. Meanwhile the leading wall 540 may include a plurality of leading surfaces, resulting in the leading edge 502 being relatively smooth.

Although the leading wall 540 is illustrated as including eight leading surfaces, it is to be appreciated that fewer or more leading surfaces may be included in the leading wall 540. For example, the leading wall 540 may range from having just one leading surface to as many leading surfaces as desired. Moreover, in some embodiments, each of the plurality of leading surfaces of the leading wall 540 may be flat or substantially flat. In other embodiments, some or all of the plurality of leading surfaces of the leading wall 540 may be curved. These and other variations are also contemplated herein and are within the scope of this disclosure.

Specific embodiments of a screw with an improved screw head according to the present invention have been described for the purpose of illustrating the manner in which the invention can be made and used. It should be understood that the implementation of other variations and modifications of this invention and its different aspects will be apparent to one skilled in the art, and that this invention is not limited by the specific embodiments described. Features described in one embodiment can be implemented in other embodiments. The subject disclosure is understood to encompass the present invention and any and all modifications, variations, or equivalents that fall within the spirit and scope of the basic underlying principles disclosed and claimed herein.

What is claimed is:

1. A screw comprising:
   a shank in between a head and a tip, the shank including
      a first portion having a first thread, a second portion having a smooth exterior surface, a third portion have a knurled surface, and a fourth portion having a smooth exterior surface, wherein:
      the first portion is provided between the second portion and the tip,
      the second portion is provided between the first portion and the third portion,
      the third portion is provided between the second portion and the fourth portion,
   wherein the head includes a plurality of protrusions provided radially along the head, wherein each of the plurality of protrusions includes a protrusion wall, a leading wall, a trailing wall, and a bottom wall.

2. The screw of claim 1, wherein the trailing wall comprises one single trailing surface.

3. The screw of claim 1, wherein the leading wall comprises a plurality of leading surfaces.

4. The screw of claim 1, wherein the bottom wall comprises a plurality of bottom surfaces.

5. The screw of claim 4, wherein at least one of the plurality of bottom surfaces is parallel to a top surface of the head.

6. The screw of claim 1, wherein the tip includes a flute.

7. The screw of claim 1, wherein the tip includes a second thread.

8. The screw of claim 7, wherein the first thread and the second thread together form one continuous thread.

9. The screw of claim 1, wherein the first thread includes a plurality of notches.

10. The screw of claim 9, wherein the plurality of notches are provided on the first thread in a helical pattern.

11. The screw of claim 1, wherein the head includes a plurality of frustoconical portions such that each successive frustoconical portion has a diameter smaller than a previous frustoconical portion.

12. The screw of claim 11, wherein the plurality of protrusions each extends downwardly from a top surface of the head and extends outwardly from at least one of the plurality of frustoconical portions.

13. The screw of claim 12, wherein a radius portion is provided in between two of the plurality of frustoconical portions.

14. The screw of claim 1, wherein the protrusion wall is frustoconical in shape with an axis that extends through a center of the screw.

\* \* \* \* \*